United States Patent [19]

Fobare et al.

[11] Patent Number: 5,187,284
[45] Date of Patent: Feb. 16, 1993

[54] N-PHENYL-N'-BENZOTHIENYLMETHYL-BIS-DIAMINO-5-METHYLENE-1,3-DIOXANE-4,6-DIONE DERIVATIVES

[75] Inventors: William F. Fobare, Hamilton, N.J.; Donald P. Strike, St. Davids, Pa.

[73] Assignee: American Home Products Corporation, New York, N.Y.

[21] Appl. No.: 914,886

[22] Filed: Jul. 22, 1992

[51] Int. Cl.$^5$ .............................................. C07D 333/56
[52] U.S. Cl. ...................................... 549/58; 549/51; 549/57
[58] Field of Search .................. 549/54, 55, 57, 58; 514/443

[56] References Cited

U.S. PATENT DOCUMENTS 4,387,105  6/1983  De Vries et al. .................. 564/50
4,387,106  6/1983  De Vries et al. .................. 564/50

FOREIGN PATENT DOCUMENTS 1147759  4/1969  United Kingdom .

OTHER PUBLICATIONS

DeVries et al. J. Med. Chem. 29, 1131 (1986).
Ross et al., *The Journal of Biological Chemistry*, 259(2), pp. 815–819 (1984).
Brown et al, *The Journal of Biological Chemistry*, 255(19), pp. 9344–9352 (1980).
Stephen, Monat, Fur Chemie, 97, 45 (1966).
Derwent Abstract 40365K, abstract of JP 58-046084 (1983).
Augustin et al., Z. Chem. 30, 169 (1990).
Augustin et al. Wiss. Univ. Halle XXXVIII 1989 M, H.3, 527–36.
Ye et al. Synthesis, pp. 317–320 (1989).
Chem. Abstract 72(23) 112900 (1969).

*Primary Examiner*—Richard L. Raymond
*Assistant Examiner*—Mark W. Russell
*Attorney, Agent, or Firm*—Richard K. Jackson

[57] ABSTRACT

A compound of the formula:

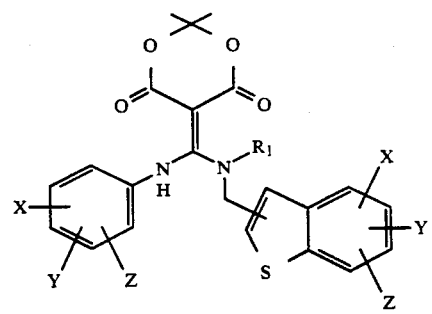

in which X, Y and Z are, independently, hydrogen, halogen, hydroxy, nitro, cyano, carboxyl, trifluoromethyl, phenyl, amino, alkylamino, dialkylamino, alkyl or alkoxy; $R_1$ is hydrogen, alkyl, alkenyl, cycloalkyl, phenyl, benzyl or substituted phenyl or benzyl or alkoxy; or a pharmaceutically acceptable salt thereof are ACAT inhibitors.

6 Claims, No Drawings

N-PHENYL-N'-BENZOTHIENYLMETHYL-BIS-DIAMINO-5-METHYLENE-1,3-DIOXANE-4,6-DIONE DERIVATIVES

BACKGROUND OF THE INVENTION

This invention relates to chemical compounds which display inhibition of Acyl-Coenzyme A: Cholesterol Acyltransferase (ACAT). Compounds of this type aid in reducing cholesterol absorption and its effect on atherosclerosis.

Atherosclerosis is the most common form of arteriosclerosis and is characterized by the buildup of phospholipids and esterified cholesterol in large and medium arteries causing them to be inelastic and thus weakened. These inelastic and occluded arteries are the most common cause of ischemic heart disease.

ACAT is an important enzyme for the intracellular esterification of cholesterol. Studies of this enzyme in cultured cells (M. S. Brown, *J. Biol. Chem.* 1980, 255, 9344) has shown that increases in ACAT activity represent increases in the presence of cholesterol laden lipoproteins. Regulation of ACAT helps prevent the absorption of cholesterol in the intestinal mucosa, and assists in the reversal of already present atherosclerotic lesions.

DESCRIPTION OF THE INVENTION

In accordance with this invention, there is provided a group of diaminomethylene dioxane dione derivatives of formula 1:

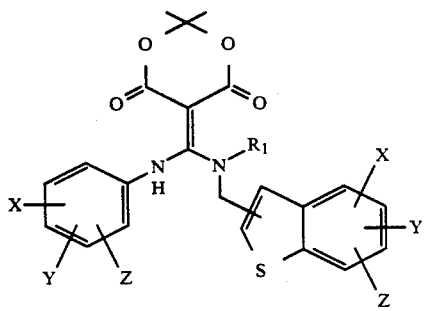

in which

X, Y and Z are, independently, hydrogen, halogen, hydroxy, nitro, cyano, carboxyl, trifluoromethyl, phenyl, amino, alkylamino of 1 to 12 carbon atoms, dialkylamino in which each alkyl group has 1 to 12 carbon atoms, alkyl of 1 to 12 carbon atoms or alkoxy of 1 to 12 carbon atoms;

$R_1$ is hydrogen, alkyl of 1 to 18 carbon atoms, alkenyl of 2 to 18 carbon atoms, cycloalkyl of 5 to 8 carbon atoms, phenyl, benzyl or substituted phenyl or benzyl where the substituents are alkyl of 1 to 12 carbon atoms or alkoxy of 1 to 12 carbon atoms;

or a pharmaceutically acceptable salt thereof.

The preferred compounds of formula 1 are those in which X, Y and Z are, independently, alkyl of 1 to 4 carbon atoms, alkoxy of 1 to 4 carbon atoms or hydroxy, and $R_1$ is alkyl of 1 to 18 carbon atoms and the benzothienyl moiety is bonded in 2 position, or a pharmaceutically acceptable salt thereof.

The halogen substituent referred to above may be chlorine, bromine, fluorine or iodine, fluorine being preferred. The pharmaceutically acceptable salts are derived from known inorganic or organic acids such as hydrochloric, hydrobromic, sulfuric, nitric, phosphoric, methanesulfonic, ethanesulfonic, hydroxyethanesulfonic, toluene sulfonic, naphthalenesulfonic, formic, acetic, propionic, oxalic, succinic, glycollic, lactic, malic, tartaric, citric, ascorbic, maleic, hydroxymaleic, pyruvic, phenylacetic, benzoic, para-amino benzoic, para-hydroxybenzoic, salicylic, sulfanilic acids, and the like.

The compounds of this invention are prepared by conversion of 2,2-dimethyl-1,3-dioxane-4,6-dione to the corresponding 5-bis-(methylthio) methylene derivative with carbon disulfide and methyl iodide in dimethylsulfoxide in the presence of a base such as triethylamine, followed by sequential displacement of the methylthio groups with the desired amines, thusly:

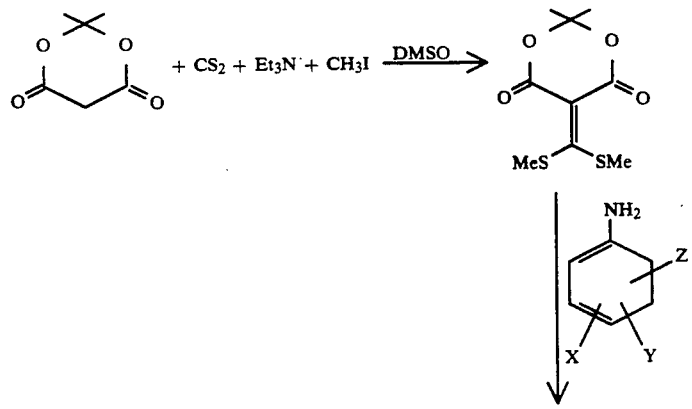

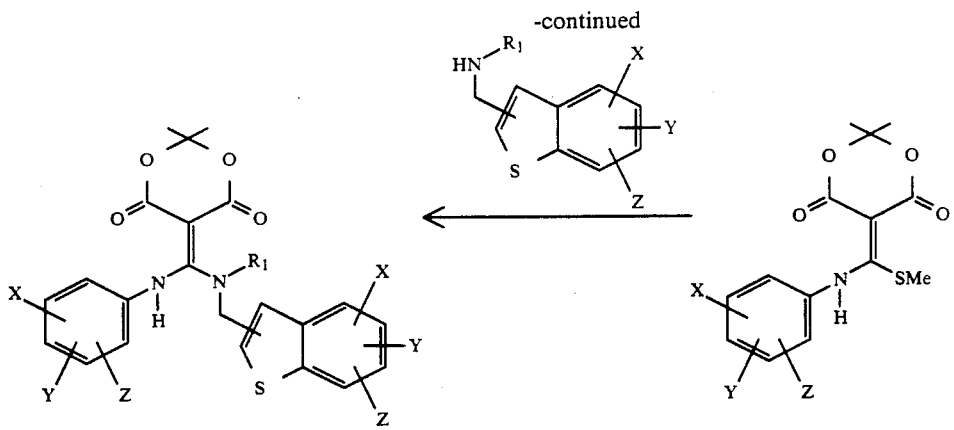

-continued

The following examples illustrate without limitation the preparation of representative compounds of this invention.

METHOD A

EXAMPLE 1

5-[(Benzo[b]thiophen-3-ylmethyl-hexyl-amino)-(3,5-di-tert-butyl-4-hydroxy-phenylamino)-methylene-2,2-dimethyl-[1,3]dioxane-4,6-dione

Procedure 1

To a solution of 7.0 g (52.16 mmol) of thianapthene in 315 mL of anhydrous diethyl ether at −78° C. was added 34 mL of 2.5M n-butyllithium dropwise. After 0.5 hours at −78° C., the solution was warmed slowly to 0° C. and a solution of 6.4 mL (52.16 mmol) of N-methylformanilide in 10 mL of diethyl ether was added dropwise. After 1.5 hours at 0° C., the reaction mixture was slowly brought to reflux for 1 hour. The mixture was cooled to room temperature and poured into 30 mL of 3N HCl. The layers were separated and the aqueous layer was extracted 3 times with 30 mL of diethyl ether. The combined ether extracts were then washed with 1N HCl (30 mL) and once with saturated aqueous NaHCO₃ (30 mL) then dried (MgSO₄) and the solvents removed at reduced pressure. The residue was dissolved in 15 mL of ethanol and 4.5 mL of saturated sodium bisulfite was added. After thorough mixing, the solution was allowed to stand at room temperature for 20 minutes. The white precipitate was filtered and washed three times with diethyl ether. After drying under vacuum, the solid was dissolved in H₂O, cooled to 0° C. and saturated Na₂CO₃ was added. This aqueous layer was extracted with ethyl acetate which was dried (MgSO₄), filtered, and the solvents were removed at reduced pressure. Column chromatography of the residue on silica gel (275 g silica gel, 93% hexanes-7% ethyl acetate to 89% hexanes-11% ethyl acetate) gave after crystallization (diethyl ether-hexanes) 1.32 g of a solid which was used without further purification or characterization.

Procedure 2

To a solution of 0.97 g (5.98 mmol) of 2-benzo[b]thiophenecarboxaldehyde, from Procedure 1, in 10 mL of methanol was added 1.81 g (17.9 mmol) of hexylamine and then methanol saturated with gaseous HCl until the pH was 7. Sodium cyanoborohydride, 0.25 g (4.18 mmol), was added as a solid and stirred at room temperature for 18 hours. The pH of the solution was lowered to 2 with concentrated HCl and the methanol was removed at reduced pressure. H₂O was added to the residue which was washed with diethyl ether. The aqueous layer was made basic with solid KOH and the solution was extracted twice with ethyl acetate. The combined ethyl acetate layers were dried (Na₂SO₄) and the solvents removed under reduced pressure. Column chromatography of the residue (120 g silica gel, 75% EtOAc-hexanes) yielded 0.55 g (37%) of a yellow oil. NMR (200 MHz, CDCL₃) δ7.8–7.63 (m 2H), 7.36–7.20 (m, 2H), 7.12 (s, 1H), 4.06 (s, 2H), 2.66 (t, 2H, J=6.4 Hz), 1.58–1.22 (m, 8H), 0.90 (t, 3H, J=6.6 Hz).

Procedure 3

To a solution of 6.4 g (25.8 mmol) of 5-[bis(methylthio)methylene]-2,2-dimethyl-1,3-dioxane-4,6-dione and 4.84 g (56.0 mmol) of sodium bicarbonate in 10 mL of degassed DMSO was added 10.0 g (36.0 mmol) of 3,5-di-t-butyl-4-hydroxyaniline hydrochloride in 30 mL of degassed DMSO over a 5 hour period at room temperature. Stirring was continued for an additional 19 hours. The reaction mixture was poured into cold H₂O and the product filtered. The solid was dried and dissolved in ethyl acetate and filtered again. The solvent was removed at reduced pressure and the residue submitted to a column chromatography on silica gel (3:1 to 2:1 hexanes-ethyl acetate) to yield 9.8 g (90%) of a solid that was used without further purification.

Procedure 4

To a solution of 0.55 g (2.22 mmol) of the amine from Procedure 2 in 20 mL CH₃CN was added 0.94 g (2.22 mmol) of the compound from Procedure 3, 0.22 g (2.22 mmol) of triethylamine and 0.36 g (1.22 mmol) of HgSO₄. The reaction mixture was allowed to reflux for 18 hours. After cooling to room temperature, the reaction mixture was filtered through Celite ® and the solvents were removed at reduced pressure. Column chromatography of the residue (110 gm silica gel, 65:35 hexanesethyl acetate) yielded after recrystallization (ethyl acetate-hexanes) 0.95 gm (69%) of a solid (m.p. 155°–159° C.). IR (KBr) 3410, 3220, 2952, 2870, 1688, 1635, 1554, 1432, 1383, 1352, 1251, 1203, 1117, 1089, 929 and 740 cm⁻¹. ¹H NMR (400 MHz, CDCl₃) δ7.76 (d, 1H, J=7.05 Hz), 7.71 (d, 1H, J=6.95 Hz), 7.35 (m, 2H), 7.24 (s, 1H), 6.95 (s, 1H), 5.23 (s, 1H), 4.69 (s, 1H), 3.09 (m, 2H), 1.69 (s, 6H), 1.63 (m, 2H), 1.35 (s, 18H), 1.26–1.19 (m, 6H), 0.83 (t, 3H, J=6.9 Hz).

Elemental analysis for C₃₆H₄₈N₂O₅S: Calc'd: C, 69.64; H, 7.79; N, 4.51; Found: C, 69.81; H, 8.09; N, 4.38.

METHOD B

EXAMPLE 2

5-[[(Benzo[b]thiophen-2-ylmethyl)-hexyl-amino]-(2,4-dimethoxyphenylamino)-methylene]-2,2-dimethyl-[1,3]dioxane-4,6-dione

Procedure 1

To a solution containing 2.0 g (8.05 mmol) of 5-[bis(-methylthio)methylene]-2.2-dimethyl-1,3-dioxane-4,6-dione in 40 mL of t-butanol, was added 1.23 g (8.05 mmol) of 2.4-dimethoxyaniline. The reaction mixture was allowed to stir at reflux for 24 hours. The mixture was cooled to room temperature and diluted with hexanes. The solid was filtered and used without further purification. Isolated: 2.3 g, 81% yield.

Procedure 2

To a solution of 0.76 g (3.08 mmol) of the amine from Method A, Procedure 2, in 15 mL of acetonitrile, was added 0.31 g (3.08 mmol) of triethylamine, 1.08 g (3.08 mmol) of the product from Procedure 1 and 0.50 g (1.69 mmol) of $HgSO_4$. The reaction mixture was allowed to stir at reflux for 18 hours. The mixture was cooled to room temperature, filtered through Celite® and the solvents removed at reduced pressure. Column chromatography (120 g silica gel, 65:35 hexanes-ethyl acetate to 50:50 hexanes-ethylacetate) of the residue yielded after recrystallization (ethyl acetate-hexanes) a yellow solid (m.p. 96°-99° C.). IR (KBr) 3430, 2960, 2925, 2860, 1697, 1632, 1572, 1512, 1456, 1437, 1386, 1347, 1312, 1208, 1158, 1079, 1032, 930 and 788 $cm^{-1}$. $^1H$ NMR (400 MHz, $CDCL_3$) δ7.79 (d, 2H, J=8.0 Hz), 7.71 (d, 1H, J=7.8 Hz), 7.33–7.28 (m, 2H), 7.25 (s, 1H), 7.14 (d, 1H, J=8.7 Hz), 6.45 (d, 1H, J=2.7 Hz), 6.30 (dd, 1H, J=2.68, 8.72 Hz), 4.70 (s, 2H), 3.75 (s, 6H), 3.07 (m, 2H), 1.64–1.56 (m, 8H), 1.22–1.12 (m, 6H), 0.80 (t, 3H, J=6.84 Hz).

Elemental analysis for $C_{30}H_{36}N_2O_6S$: Calc'd: C, 65.20; H, 6.57; N, 5.07; Found: C, 64.85; H, 6.58; N, 5.02.

EXAMPLE 3

5-[[Benzo[b]thiophen-2-ylmethyl-(1-methyl-hexyl)-amino]-(2,4-dimethoxy-phenylamino)-methylene-2,2-dimethyl-[1,3]dioxane-4,6-dione This compound was synthesized using the methodology described in Method B except 2-aminoheptane was substituted for hexylamine to yield a white solid (m.p. 167° C.).

Elemental analysis for $C_{31}H_{38}N_2O_6S$: Calc'd: C, 65.70; H, 6.76; N, 4.94; Found: C, 65.64; H, 6.67; N, 4.84.

EXAMPLE 4

5-[[Benzo[b]thiophen-2-ylmethyl-(1-methyl-hexyl)-amino]-(3,5-di-tert-butyl-4-hydroxy-phenylamine)-methylene-2,2-dimethyl-[1,3]dioxane-4,6-dione This compound was synthesized using the methodology described in Method A except 2-aminoheptane was substituted for hexylamine to yield a white solid (m.p. 195°-197° C.).

Elemental analysis for $C_{37}H_{50}N_2O_5S$: Calc'd: C, 70.00; H, 7.94; N, 4.41; Found: C, 70.21; H, 7.85; N, 4.46.

The ability of the compounds of this invention to inhibit acyl-coenzyme A: cholesterol acyltransferase was established by initially showing that they inhibited intracellular cholesterol esterification by subjecting them to the standard experimental test procedure of Ross et al., *J. Biol. Chem.* 259 815 (1984). The results of these studies are presented in:

| Example | In Vitro % Inhib. (Concentration-μM) | $IC_{50}$ (μM) |
| --- | --- | --- |
| 1 | 98 (25) | 0.38 |
| 2 | 94 (25) | 0.62 |
| 3 | 97 (25) | 0.35 |
| 4 | 98 (25) | 0.31 |

From these data, the ability of the compounds to inhibit ACAT is clearly established. Hence, the compounds of this invention are useful in the treatment of those disease states which are amenable to treatment by reduction of the rate of cholesterol esterification, the rate of accumulation and deposits of cholesteryl esters on arterial walls and the rate of formation of atheromatous lesions. As such, the anti-atherosclerotic agents of this invention may be administered to a mammal in need of intracellular cholesteryl ester concentration reduction orally or parenterally in an amount sufficient to inhibit ACAT catalysis of cholesterol esterification.

The compounds of this invention may be administered by themselves or in combination with pharmaceutically acceptable liquid or solid carriers. Oral administration in conventional formulations as tablets, capsules, powders, or suspensions is preferred.

A solid carrier can include one or more substances which may also act as flavoring agents, lubricants, solubilisers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both of pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g., glycols) and their derivatives, and oils (e.g. fractionated coconut oil and arachis oil). For parenteral administration, the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular intraperitoneal or subcutaneous injection. Sterile solutions can also be administered intravenously. When the compound is orally active, it can be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific hypercholesterolemic/atherosclerotic condition must be subjectively determined by the attending physician. The variables involved include the extent of the disease state, size, age and response pattern of the patient.

What is claimed is:

1. A compound of the formula:

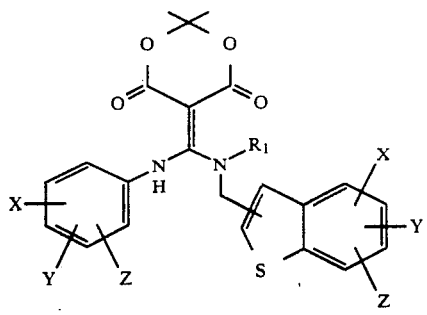

in which
X, Y and Z are, independently, hydrogen, halogen, hydroxy, nitro, cyano, carboxyl, trifluoromethyl, phenyl, amino, alkylamino of 1 to 12 carbon atoms, dialkylamino in which each alkyl group has 1 to 12 carbon atoms, alkyl of 1 to 12 carbon atoms or alkoxy of 1 to 12 carbon atoms;

$R_1$ is hydrogen, alkyl of 1 to 18 carbon atoms, alkenyl of 2 to 18 carbon atoms, cycloalkyl of 5 to 8 carbon atoms, phenyl, benzyl or substituted phenyl or benzyl where the substituents are alkyl of 1 to 12 carbon atoms or alkoxy of 1 to 12 carbon atoms;

or a pharmaceutically acceptable salt thereof.

2. A compound of claim 1 in which X, Y and Z are, independently, alkyl of 1 to 4 carbon atoms, alkoxy of 1 to 4 carbons atoms or hydroxy; $R_1$ is alkyl of 1 to 18 carbon atoms and the benzothienyl moiety is bonded in 2 position, or a pharmaceutically acceptable salt thereof.

3. A compound of claim 1 which is 5-[(benzo[b]thiophen-3-ylmethyl-hexylamino)-(3,5-di-tert-butyl-4-hydroxy-phenylamino)-methylene-2,2-dimethyl-[1,3]dioxane-4,6-dione, or a pharmaceutically acceptable salt thereof.

4. A compound of claim 1 which is 5-[[(benzo[b]thiophen-2-ylmethyl)-hexylamino]-(2,4-dimethoxy-phenylamino)-methylene]-2,2-dimethyl-[1,3]dioxane-4,6-dione, or a pharmaceutically acceptable salt thereof.

5. A compound of claim 1 which is 5-[[benzo[b]thiophen-2-ylmethyl-(1-methyl-hexyl)-amino]-(2,4-dimethoxy-phenylamino)-methylene-2,2-dimethyl-[1,3]dioxane-4,6-dione, or a pharmaceutically acceptable salt thereof.

6. A compound of claim 1 which is 5-[[benzo[b]thiophen-2-ylmethyl-(1-methyl-hexyl)-amino]-(3,5-di-tert-butyl-4-hydroxy-phenylamine)-methylene-2,2-dimethyl-[1,3]dioxane-4,6-dione, or a pharmaceutically acceptable salt thereof.

* * * * *